(12) United States Patent
Takahashi et al.

(10) Patent No.: US 10,864,701 B2
(45) Date of Patent: Dec. 15, 2020

(54) STRETCHABLE CONDUCTIVE FILM FOR TEXTILES

(71) Applicant: TATSUTA ELECTRIC WIRE & CABLE CO., LTD., Osaka (JP)

(72) Inventors: Akio Takahashi, Kyoto (JP); Tsunehiko Terada, Kyoto (JP)

(73) Assignee: TATSUTA ELECTRIC WIRE & CABLE CO., LTD., Osaka (JP)

( * ) Notice: Subject to any disclaimer, the term of this patent is extended or adjusted under 35 U.S.C. 154(b) by 219 days.

(21) Appl. No.: 15/779,579

(22) PCT Filed: Oct. 19, 2016

(86) PCT No.: PCT/JP2016/080986
§ 371 (c)(1),
(2) Date: May 29, 2018

(87) PCT Pub. No.: WO2017/094384
PCT Pub. Date: Jun. 8, 2017

(65) Prior Publication Data
US 2020/0086606 A1 Mar. 19, 2020

(30) Foreign Application Priority Data
Nov. 30, 2015 (JP) .................... 2015-233710

(51) Int. Cl.
*B32B 7/025* (2019.01)
*C09J 7/35* (2018.01)
(Continued)

(52) U.S. Cl.
CPC ............ *B32B 7/025* (2019.01); *A61B 5/6803* (2013.01); *B32B 7/06* (2013.01); *B32B 7/12* (2013.01);
(Continued)

(58) Field of Classification Search
CPC .. B32B 7/025; B32B 7/06; B32B 7/12; B32B 27/20; B32B 27/40; B32B 2264/105;
(Continued)

(56) References Cited

U.S. PATENT DOCUMENTS 6,265,460 B1  7/2001  Kawate
7,033,668 B2  4/2006  Schümann
(Continued)

FOREIGN PATENT DOCUMENTS

CN  102016148 A  4/2011
CN  103959396 A  7/2014
(Continued)

OTHER PUBLICATIONS

M. Burrows, "Printed Wearables, Electronic Inks for the Wearable World", Dupont, Inc, 2014, pp. 1-14, Printed Electronics USA; English text.
(Continued)

*Primary Examiner* — Patricia L. Nordmeyer
(74) *Attorney, Agent, or Firm* — Rankin, Hill & Clark LLP

(57) ABSTRACT

A stretchable conductive film for textiles 1 includes a stretchable conductive layer 3, and a hot-melt adhesive agent layer 4 formed on one surface of the stretchable conductive layer 3. The stretchable conductive film for textiles 1 may also include a first peel film 2 formed on a surface of the stretchable conductive layer 3 on the opposite side from the hot-melt adhesive agent layer 4 side, and a second peel film 5 formed on a surface of the hot-melt adhesive agent layer 4 on the opposite side from the stretchable conductive layer 3 side.

9 Claims, 15 Drawing Sheets

(51) Int. Cl.
| | |
|---|---|
| B32B 27/20 | (2006.01) |
| C09J 9/02 | (2006.01) |
| H01B 1/22 | (2006.01) |
| C09J 7/40 | (2018.01) |
| C09J 7/20 | (2018.01) |
| B32B 27/40 | (2006.01) |
| A61B 5/00 | (2006.01) |
| B32B 7/06 | (2019.01) |
| B32B 7/12 | (2006.01) |
| A61B 5/0402 | (2006.01) |
| A61B 5/0488 | (2006.01) |

(52) U.S. Cl.
CPC .............. *B32B 27/20* (2013.01); *B32B 27/40* (2013.01); *C09J 7/203* (2018.01); *C09J 7/35* (2018.01); *C09J 7/405* (2018.01); *C09J 9/02* (2013.01); *H01B 1/22* (2013.01); *A61B 5/0402* (2013.01); *A61B 5/0488* (2013.01); *B32B 2264/105* (2013.01); *B32B 2307/202* (2013.01); *C09J 2203/326* (2013.01); *C09J 2301/41* (2020.08)

(58) Field of Classification Search
CPC ....... B32B 2307/202; C09J 7/35; C09J 7/405; C09J 7/203; C09J 9/02; C09J 2203/326; C09J 2205/106; A61B 5/6803; A61B 5/0402; A61B 5/0488; H01B 1/22
See application file for complete search history.

(56) References Cited

U.S. PATENT DOCUMENTS

| | | | |
|---|---|---|---|
| 2011/0065217 A1* | 3/2011 | Terada | H01L 21/6836 438/17 |
| 2011/0070409 A1 | 3/2011 | Nishimaki | |
| 2015/0310954 A1 | 10/2015 | Liu et al. | |
| 2016/0372230 A1 | 12/2016 | Imahashi | |
| 2017/0066225 A1 | 3/2017 | Chen et al. | |
| 2017/0194073 A1 | 7/2017 | Takahashi et al. | |
| 2018/0020936 A1 | 1/2018 | Kwon et al. | |

FOREIGN PATENT DOCUMENTS

| | | |
|---|---|---|
| CN | 104538088 A | 4/2015 |
| CN | 105047252 A | 11/2015 |
| EP | 2924695 A1 | 9/2015 |
| JP | H09-092032 A | 4/1997 |
| JP | 2000017242 A | 1/2000 |
| JP | 2004176005 A | 6/2004 |
| JP | 2009138141 A | 6/2009 |
| JP | 2012211256 A | 11/2012 |
| JP | 2014108134 A | 6/2014 |
| JP | 2014162124 A | 9/2014 |
| JP | 2016141713 A | 8/2016 |
| KR | 10-2011-0044732 A | 4/2011 |
| TW | 201446936 A | 12/2014 |
| WO | 2015005204 A1 | 1/2015 |
| WO | 2015/162545 A1 | 10/2015 |
| WO | 2016017644 A1 | 2/2016 |
| WO | 2016114298 A1 | 7/2016 |

OTHER PUBLICATIONS

Notice of Submission of Publications for the corresponding Japanese Patent Application No. 2015-233710 dated Sep. 5, 2019.
Y. Cheng et al. "Copper nanowire based transparent conductive films with high stability and superior stretchability," Journal of Materials Chemistry C, 2014, p. 5309-5316, vol. 2, Royal Society of Chemistry, United Kingdom; Cited in European Search Report.
A. Santamaria et al. "Electrically Conductive Adhesives with a Focus on Adhesives that Contain Carbon Nanotubes," Journal of Applied Polymer Science, 2013, p. 1643-1652, vol. 129 issue 4, Wiley Periodicals, Inc., USA; Cited in European Search Report.
K.Y. Chun et al. "Highly conductive, printable and stretchable composite films of carbon nanotubes and silver," Nature Nanotechnology, 2010, p. 1-14, vol. 5 No. 12 Supplementary Information, Springer Nature, USA; Cited in European Search Report.
European Search Report dated Jun. 6, 2019 for the corresponding EP Patent Application No. 16870324.7.
International Search Report dated Jan. 17, 2017 filed in PCT/JP2016/080986.
Osman et al., "Textile UWB Antenna Bending and Wet Performances", International Journal of Antennas and Propagation, 2012, vol. 2012, Article ID 251682, doi:10.1155/2012/251682, pp. 1-12, total 14 pages; cited in CNOA.
Chinese Office Action (CNOA) dated Apr. 26, 2020 for the corresponding Chinese Patent Application No. 2016800696541.
Korean Office Action (KROA) dated Apr. 29, 2020 for the corresponding Korean Patent Application No. 10-2018-7016379.
Taiwanese Office Action (TWOA) dated May 6, 2020 for the corresponding Taiwanese Patent Application No. 105135088.

* cited by examiner

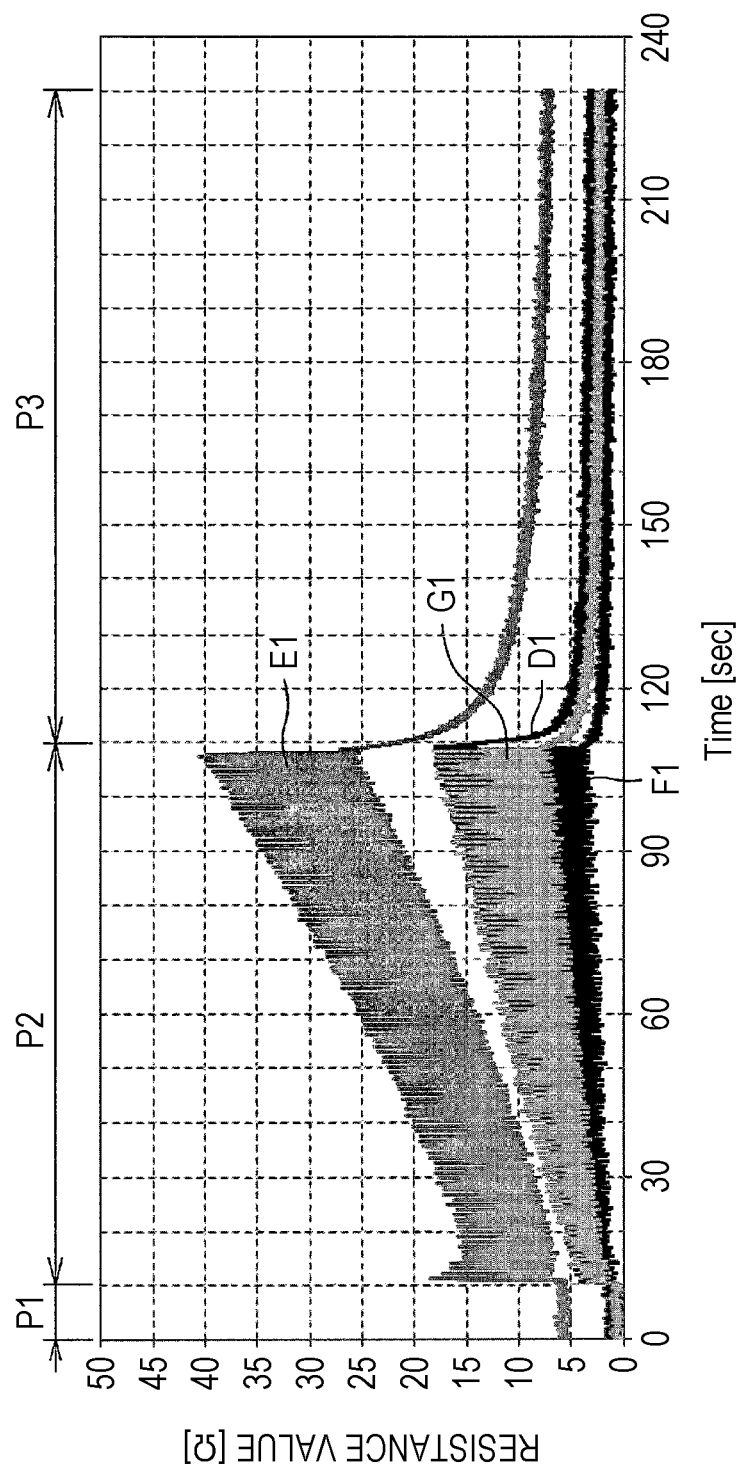

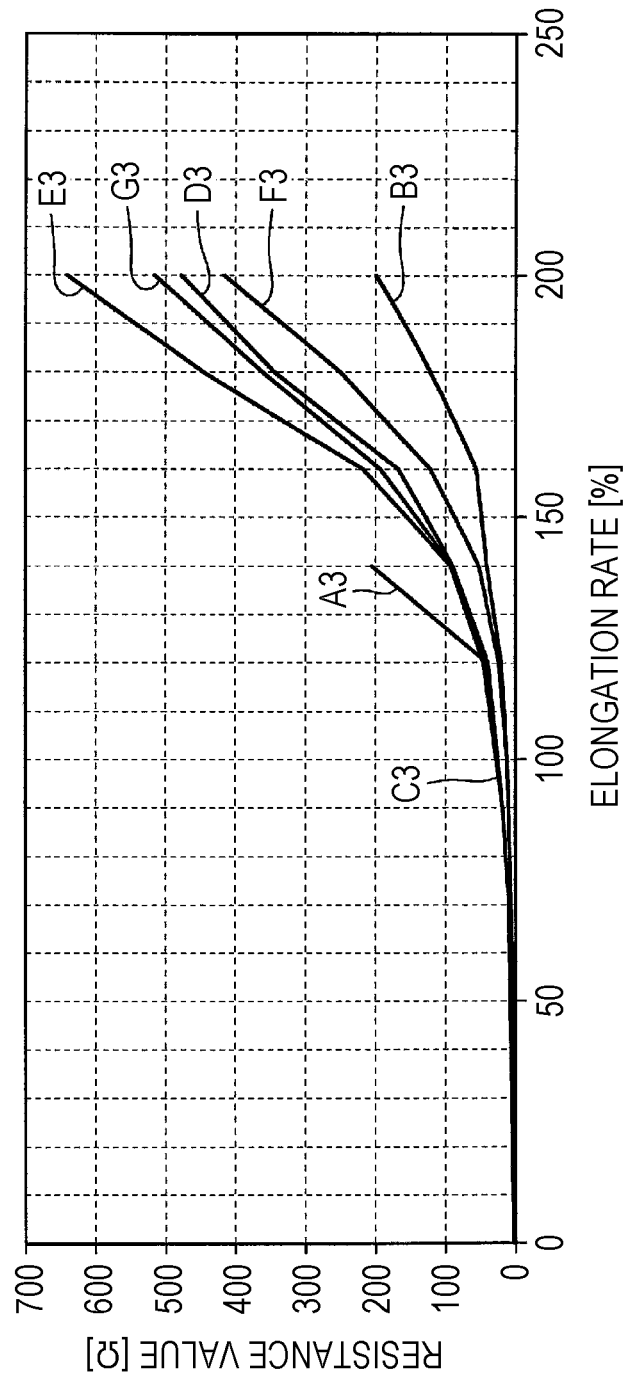

STRETCHABLE CONDUCTIVE FILM FOR TEXTILES

TECHNICAL FIELD

The present invention relates to a stretchable conductive film for textiles which may be used as an electrode and wiring material for measuring biometric information.

BACKGROUND ART

Techniques for electronically measuring human biometric information using textile-type wearable devices are gaining attention. Here, the textile-type wearable devices refer to devices that can take measurements or be operated while being worn as a garment. As a material of the textile-type wearable devices, fibers coated with highly conductive resin have been developed.

CITATION LIST

Patent Literature

Patent Literature 1: JP-A-2014-162124

SUMMARY OF THE INVENTION

Problems to be Solved by the Invention

An object of the present invention is to provide a stretchable conductive film for textiles as described below. The conductive film can be easily attached to textile fabric, and has electrical conductivity and stretch properties.

Solutions to the Problems

A stretchable conductive film for textiles according to the present invention includes a stretchable conductive layer having stretch properties, and a hot-melt adhesive agent layer formed on one surface of the stretchable conductive layer. The stretchable conductive layer is configured from a conductive composition including an elastomer and a conductive filler filling the elastomer.

In this configuration, the stretchable conductive film for textiles (hereinafter referred to as "stretchable conductive film") may be attached to a textile fabric as follows, for example. First, the stretchable conductive film is cut to a shape in accordance with the purpose of use. Then, the stretchable conductive film is placed on the textile fabric in such a way that the surface of the stretchable conductive film on the side of the hot-melt adhesive agent layer opposes the textile fabric. Then, an iron or the like is used to thermally bond the stretchable conductive film to the textile fabric. In this way, the stretchable conductive film including the stretchable conductive layer and the hot-melt adhesive agent layer is placed in a state of being attached to the textile fabric.

That is, in this configuration, the stretchable conductive film for textiles can be obtained which can be easily attached to the textile fabric. The stretchable conductive layer includes the conductive composition having an elastomer and a conductive filler filling the elastomer. Therefore, the stretchable conductive film for textiles as attached to the textile fabric is electrically conductive and has stretch properties.

An embodiment of the present invention further includes a peel film formed on a surface of the hot-melt adhesive agent layer on the opposite side from the stretchable conductive layer side.

An embodiment of the present invention further includes a first peel film formed on a surface of the stretchable conductive layer on the opposite side from the hot-melt adhesive agent layer side; and a second peel film formed on a surface of the hot-melt adhesive agent layer on the opposite side from the stretchable conductive layer side.

An embodiment of the present invention further includes a stretchable protection layer having stretch properties and formed on at least a part of a surface of the stretchable conductive layer on the opposite side from the hot-melt adhesive agent layer side.

An embodiment of the present invention further includes a stretchable protection layer having stretch properties and formed on at least a part of the surface of the stretchable conductive layer on the opposite side from the hot-melt adhesive agent layer side, and a peel film formed on a surface of the hot-melt adhesive agent layer on the opposite side from the stretchable conductive layer side.

An embodiment of the present invention further includes a stretchable protection layer having stretch properties and formed on at least a part of the surface of the stretchable conductive layer on the opposite side from the hot-melt adhesive agent layer side; a first peel film formed on the surface of the stretchable conductive layer on the opposite side from the hot-melt adhesive agent layer side so as to cover the stretchable protection layer; and a second peel film formed on the surface of the hot-melt adhesive agent layer on the opposite side from the stretchable conductive layer side.

In an embodiment of the present invention, the conductive filler is dendritic.

In an embodiment of the present invention, the conductive filler is a dendritic silver powder.

In an embodiment of the present invention, the conductive filler is a silver-coated copper powder including a dendritic copper powder coated with silver.

In an embodiment of the present invention, the conductive filler has a coil shape.

The above and other purposes, features, and effects of the present invention will become apparent from the following description of embodiments with reference made to the attached drawings.

BRIEF DESCRIPTION OF THE DRAWINGS

FIG. 3C is a graph illustrating changes in the resistance values of samples d1, e1, f1, and g1 when a 20% tensile strain was applied to mainly the samples d1, e1, f1, and g1 repeatedly 100 times at a frequency of 1.0 Hz.

FIG. 5A is a graph illustrating the resistance values relative to elongation rates of samples a3, b3, c3, d3, e3, f3, and g3 when the samples a3, b3, c3, d3, e3, f3, and g3 were elongated at a plurality of different elongation rates.

DESCRIPTION OF EMBODIMENTS

Figure 1:
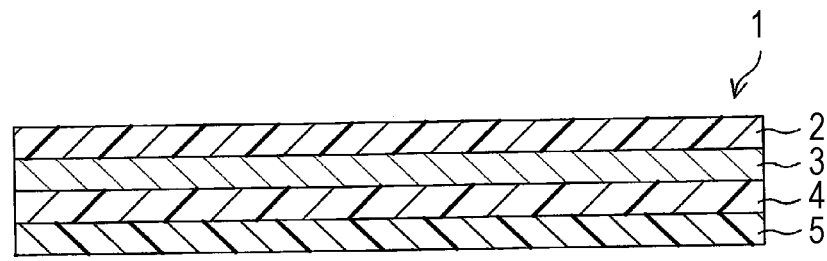
FIG. 1 is a schematic cross sectional view illustrating a configuration of a stretchable conductive film for textiles according to the first embodiment of the present invention.

FIG. 1 is a schematic cross sectional view illustrating a configuration of a stretchable conductive film for textiles according to the first embodiment of the present invention.

The stretchable conductive film for textiles (hereafter simply referred to as "stretchable conductive film 1") includes a first peel film (transfer film) 2, a stretchable conductive layer 3, a hot-melt adhesive agent layer 4, and a second peel film (protection film) 5. The stretchable conductive layer 3 is formed on one surface of the first peel film 2. The hot-melt adhesive agent layer 4 is formed on a surface of the stretchable conductive layer 3 on the opposite side from the first peel film 2 side. The second peel film 5 is formed on a surface of the hot-melt adhesive agent layer 4 on the opposite side from the stretchable conductive layer 3 side. The stretchable conductive film 1 is sheet-shaped. The stretchable conductive film 1 may have an elongate shape longer in one direction.

As the first peel film 2, examples that may be used include peel paper (release paper); fluorine films; polyethylene naphthalate (PEN) films having a silicone-based or non-silicone-based (such as melamine-based or acrylic-based) mold-release agent applied to one or both surfaces thereof; and polyethylene terephthalate (PET) films. As the second peel film 5, examples similar to those of the first peel film 2 may be used.

Examples of the material of the hot-melt adhesive agent used for the hot-melt adhesive agent layer 4 include thermoplastic resins, such as polyesters, polyurethanes, polyamides, olefins, and ethylene-vinyl acetates. In the present invention, the hot-melt adhesive agent preferably has a melting point of not more than 130° C., durometer hardness of not more than 95 A, and rupture elongation of not less than 300%, and more preferably a melting point of not more than 120° C., durometer hardness of not more than 85 A, and rupture elongation of not less than 500%. More specifically, as the hot-melt adhesive agent, a polyurethane-based thermoplastic resin may be used, such as "SHM101-PUR" (product name) manufactured by Sheedom Co., Ltd.

The stretchable conductive layer 3 is configured from a conductive composition including an elastomer and a conductive filler filling the elastomer.

The elastomer is an elastic resin, such as a styrene-based elastomer, an olefin-based elastomer, a polyester-based elastomer, a polyurethane-based elastomer, a polyamide-based elastomer, and a silicone-based elastomer. A polyurethane-based elastomer is configured from a hard segment and a soft segment. Examples of the soft segment include carbonates, esters, and ethers. The soft segment, in terms of physical properties, preferably has 100% modulus of 2 to 20 MPa, rupture strength of 40 to 90 MPa, rupture elongation of 300 to 500%, permanent strain of not more than 20%, and a thermal softening point of not less than 150° C., and more preferably 100% modulus of 3 to 10 MPa, rupture strength of 50 to 75 MPa, rupture elongation of 350 to 450%, permanent strain of not more than 10%, and a thermal softening point of not less than 170° C.

Specific examples that may be used include NE-8880, MAU-9022, NE-310, NE-302HV, and CU-8448 manufactured by Dainichiseika Color & Chemicals Mfg. Co., Ltd. As a polyurethane-based elastomer, PANDEX 372E manufactured by DIC corporation may be used. The elastomer may comprise a single resin, or may include a plurality of kinds of resin. The elastomer, from the viewpoint of improving manufacturability (processability), flexibility and the like, may include an additive such as a plasticizer, a processing aid, a cross-linker, a vulcanization accelerator, a vulcanization aid, an anti-oxidant, a softener, and a coloring agent.

The shape of the conductive filler may be dendritic, coiled, clumpy, spherical, flaky, needle-like, fibrous, or the like. A dendritic shape refers to a shape in which bar-shaped separating branches extend in 2-dimensional directions or 3-dimensional directions from a bar-shaped main branch. A dendritic shape include a shape in which the separating branches are bent in the middle, and a shape in which additional bar-shaped separating branches extend from the middle of the separating branches.

A dendritic conductive filler will be described. The dendritic conductive filler may be a dendritic copper powder or silver powder, for example. The dendritic conductive filler may be a silver-coated copper powder comprising a dendritic copper powder with a silver coating, or a gold-coated copper powder comprising a dendritic copper powder with a gold coating. When the conductive filler is made from a dendritic silver-coated copper powder, a conductive filler which can be obtained is relatively inexpensive, has a resistance value close to that of a conductive filler made from silver, and has excellent electrical conductivity and migration resistance. When the conductive filler is made from a dendritic copper powder, a conductive filler can be obtained which is inexpensive and yet has a low resistance value.

When the conductive filler is made from a dendritic silver-coated copper powder, a polyurethane-based elastomer is preferably adopted as the elastomer. In this case, polyurethane-based elastomers have a volume resistivity of 10E+11 to 13 Ωcm, which is lower than that of other elastomers by approximately two orders of magnitude, and have high affinity with respect to a silver-containing conductive filler. Accordingly, the polyurethane-based elastomer enables the conductive composition to stretch well.

The conductive filler has a grain size lower limit of 1 μm, or preferably 2 μm. When the lower limit is not less than 1 μm, the conductive filler grains are more likely to contact each other, and the conductivity of the conductive composition is improved. The conductive filler has a grain size upper limit of 20 μm, or preferably 10 μm. When the upper limit is not more than 20 μm, it becomes possible to decrease the thickness of the conductive layer made from the conductive composition.

When the conductive filler has a coil shape (including a helix shape and a spiral shape), the conductive filler, upon stretching of the elastomer, extends as if a coil were pulled. Thus, even when the elastomer is stretched, an increase in the resistance value of the conductive composition can be suppressed. In this way, it becomes possible to provide a conductive composition that has stretch properties and that can suppress an increase in resistance value when stretched.

Examples of Stretchable Conductive Layer

Examples of the stretchable conductive layer 3 will be described.

Table 1 indicates Examples 1 to 7 of the stretchable conductive layer 3.

TABLE 1

| | Conductive filler | | | | | |
|---|---|---|---|---|---|---|
| | Type | Filling factor (mass %) | Elastomer | Length L (cm) | Width W (cm) | Thickness T (cm) |
| Sample a1 | Silver-coated copper | 60 | Pandex 372E | 15.0 | 1.0 | 0.008 |
| Sample a2 | Silver-coated copper | 60 | Pandex 372E | 7.5 | 1.0 | 0.008 |
| Sample a3 | Silver-coated copper | 60 | Pandex 372E | 5.0 | 1.0 | 0.008 |
| Sample b1 | Silver-coated copper | 80 | Pandex 372E | 15.0 | 1.0 | 0.008 |
| Sample b2 | Silver-coated copper | 80 | Pandex 372E | 7.5 | 1.0 | 0.008 |
| Sample b3 | Silver-coated copper | 80 | Pandex 372E | 5.0 | 1.0 | 0.008 |
| Sample c1 | Silver-coated copper | 90 | Pandex 372E | 15.0 | 1.0 | 0.008 |
| Sample c2 | Silver-coated copper | 90 | Pandex 372E | 7.5 | 1.0 | 0.008 |
| Sample c3 | Silver-coated copper | 90 | Pandex 372E | 5.0 | 1.0 | 0.008 |
| Sample d1 | Silver-coated copper | 80 | NE-310 | 15.0 | 1.0 | 0.006 |
| Sample d3 | Silver-coated copper | 80 | NE-310 | 5.0 | 1.0 | 0.006 |
| Sample e1 | Silver-coated copper | 80 | NE-310 | 15.0 | 1.0 | 0.004 |
| Sample e3 | Silver-coated copper | 80 | NE-310 | 5.0 | 1.0 | 0.004 |
| Sample f1 | Silver | 80 | NE-310 | 15.0 | 1.0 | 0.006 |
| Sample f3 | Silver | 80 | NE-310 | 5.0 | 1.0 | 0.006 |
| Sample g1 | Silver | 80 | NE-310 | 15.0 | 1.0 | 0.004 |
| Sample g3 | Silver | 80 | NE-310 | 5.0 | 1.0 | 0.004 |

Example 1 of Stretchable Conductive Layer

In a polyurethane-based elastomer (PANDEX 372E manufactured by DIC corporation), a dendritic silver-coated copper powder with an average grain size of 5 μm (manufactured by MITSUI MINING & SMELTING CO., LTD.) was blended such that the filling factor of the silver-coated copper powder (filling factor of the conductive filler in the conductive composition) became 80 mass %. Then, to 100 parts by mass of the polyurethane-based elastomer, 40 parts by mass of a mixed solvent of isopropyl alcohol and toluene (isopropyl alcohol to toluene weight ratio 5:5) was added and stirred using a planetary mixer. In this way, a solution containing the polyurethane-based elastomer, the silver-coated copper powder, and organic solvent (hereinafter referred to as "conductive solution") was obtained.

Then, the conductive solution was applied to one surface of a peel film using an applicator so that the film thickness after drying became 80 μm, and heated to dry. The heating and drying step involved heating and drying with hot air at 60° C., heating and drying with hot air at 100° C., and heating and drying with hot air at 120° C., each for two minutes. In this way, a thin film of conductive composition (hereinafter referred to as "conductive layer") was formed on one surface of the peel film.

The conductive layer was cut to a predetermined size, and then the peel film was peeled from the conductive layer. In this way, samples b1, b2, and b3 of the stretchable conductive layer 3 were obtained.

Example 2 of Stretchable Conductive Layer

A conductive layer was formed on one surface of a peel film in the same way as in Example 1, with the exception that in the polyurethane-based elastomer, a dendritic silver-coated copper powder was blended so that the filling factor of the silver-coated copper powder became 90 mass %, and that the mixed solvent was 164 parts by mass with respect to 100 parts by mass of the polyurethane-based elastomer. After the conductive layer was cut to a predetermined size, the peel film was peeled from the conductive layer. In this way, samples c1, c2, and c3 of the stretchable conductive layer 3 were obtained.

Example 3 of Stretchable Conductive Layer

A conductive layer was formed on one surface of a peel film in the same way as in Example 1, with the exception that in the polyurethane-based elastomer, the dendritic silver-coated copper powder was blended so that the filling factor of the silver-coated copper powder became 60 mass %, and that no mixed solvent was used. After the conductive layer was cut to a predetermined size, the peel film was peeled from the conductive layer. In this way, samples a1, a2, and a3 of the stretchable conductive layer 3 were obtained.

Example 4 of Stretchable Conductive Layer

In a polyurethane-based elastomer (NE-310 manufactured by Dainichiseika Color & Chemicals Mfg. Co., Ltd.), a dendritic silver-coated copper powder with an average grain size of 5 μm (manufactured by MITSUI MINING & SMELTING CO., LTD.) was blended such that the filling factor of the silver-coated copper powder (filling factor of the conductive filler in the conductive composition) became 80 mass %. Then, to 100 parts by mass of the polyurethane-based elastomer, 40 parts by mass of a mixed solvent of isopropyl alcohol and toluene (isopropyl alcohol to toluene weight ratio 5:5) was added and stirred using a planetary mixer. In this way, a solution containing the polyurethane-based elastomer, the silver-coated copper powder, and organic solvent (hereinafter referred to as "conductive solution") was obtained.

Then, the conductive solution was applied to one surface of a peel film using an applicator so that the film thickness after drying became 60 μm, and heated to dry. The heating and drying step involved heating and drying with hot air at 60° C., heating and drying with hot air at 100° C., and heating and drying with hot air at 120° C., each for two minutes. In this way, a thin film of conductive composition (hereinafter referred to as "conductive layer") was formed on one surface of the peel film.

After the conductive layer was cut to a predetermined size, the peel film was peeled from the conductive layer. In this way, samples d1 and d3 of the stretchable conductive layer 3 were obtained.

Example 5 of Stretchable Conductive Layer

A conductive layer was formed on one surface of a peel film in the same way as in Example 4 with the exception that the conductive solution was applied to the one surface of the peel film so that the film thickness after drying became 40 μm. After the conductive layer was cut to a predetermined size, the peel film was peeled from the conductive layer. In this way, samples e1 and e3 of the stretchable conductive layer 3 were obtained.

Example 6 of Stretchable Conductive Layer

In a polyurethane-based elastomer (NE-310 manufactured by Dainichiseika Color & Chemicals Mfg. Co., Ltd.), a dendritic silver powder (manufactured by MITSUI MINING & SMELTING CO., LTD.) with an average grain size of 5 μm was blended such that the filling factor of the silver powder (filling factor of the conductive filler in the conductive composition) became 80 mass %. Then, with respect to 100 parts by mass of the polyurethane-based elastomer, 40 parts by mass of a mixed solvent of isopropyl alcohol and toluene (isopropyl alcohol to toluene weight ratio 5:5) was added and stirred using a planetary mixer. In this way, a solution containing the polyurethane-based elastomer, the silver powder, and organic solvent (hereinafter referred to as "conductive solution") was obtained.

Then, the conductive solution was applied to one surface of a peel film using an applicator so that the film thickness after drying became 60 μm, and heated to dry. The heating and drying step involved heating and drying with hot air at 60° C., heating and drying with hot air at 100° C., and heating and drying with hot air at 120° C., each for two minutes. In this way, a thin film of conductive composition (hereinafter referred to as "conductive layer") was formed on one surface of the peel film.

After the conductive layer was cut to a predetermined size, the peel film was peeled from the conductive layer. In this way, samples f1 and f3 of the stretchable conductive layer 3 were obtained.

Example 7 of Stretchable Conductive Layer

A conductive layer was formed on one surface of a peel film in the same way as in Example 6, with the exception that the conductive solution was applied to the one surface of the peel film so that the film thickness after drying became 40 μm. After the conductive layer was cut to a predetermined size, the peel film was peeled from the conductive layer. In this way, samples g1 and g3 of the stretchable conductive layer 3 were obtained.

Figure 2:
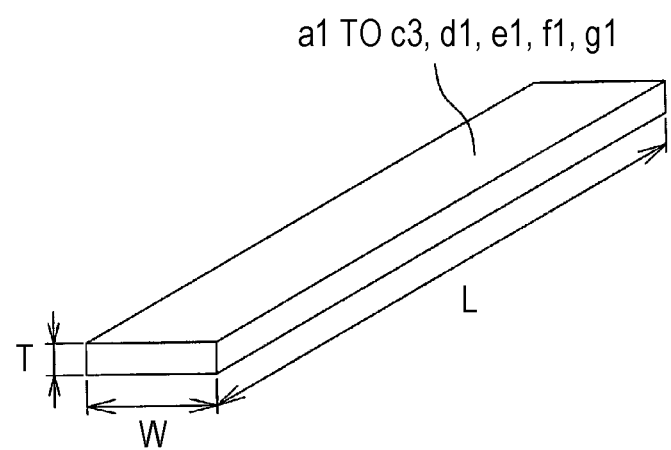
FIG. 2 is a schematic perspective view for describing the shape of a sample of a stretchable conductive layer.

Table 1 shows the filling factor of the conductive filler in each of the samples obtained as described above, and the length L, width W, and thickness T of the samples. FIG. 2 is a schematic diagram of the shape of each sample. As illustrated in FIG. 2, the shape of each sample is rectangular band-like as viewed in plan. In FIG. 2, L is the sample length, W is the sample width, and T is the sample thickness.

[First Evaluation Experiment]

With respect to the samples a1, b1, c1, d1, e1, f1, and g1, a first evaluation experiment was conducted. In the first evaluation experiment, the samples were initially mounted to a home-built fatigue testing machine. Here, the home-built fatigue testing machine had a pair of acrylic plates of 30 centimeters square that was capable of executing reciprocating motion in opposite directions. Ends of the samples were respectively fastened to the surface of the acrylic plates, and the ends were further pinched by alligator clips and connected to an electric resistance measuring device. Then, the samples were maintained in natural state for 10 seconds. The period may be referred to as a first period P1. Thereafter, a 20% tensile strain was applied to the samples repeatedly 100 times at a frequency of 1.0 Hz. This period may be referred to as a second period P2. The second period P2 was 100 seconds. Finally, the samples were again maintained in natural state for 120 seconds. This period may be referred to as a third period P3. During each of these periods, the resistance between the ends of the samples was measured.

The 20% tensile strain refers to a tensile strain such that the stretch rate r of the samples becomes 20%. When the length of the sample before being stretched is L1, the length of the sample after being stretched is L2, and an increase in length L2 after a stretch with respect to the length L1 of the sample before being stretched is ΔL (=L−L1), the stretch rate r is expressed by the following expression (1).

$$r=(\Delta L/L1)\times 100 \quad (1)$$

The length L1 before stretch of the samples a1, b1, c1, d1, e1, f1, and g1 was 15 cm. Accordingly, when the 20% tensile strain was applied, the length of the samples a1, b1, c1, d1, e1, f1, and g1 after a stretch became 18 cm.

Figure 3A:
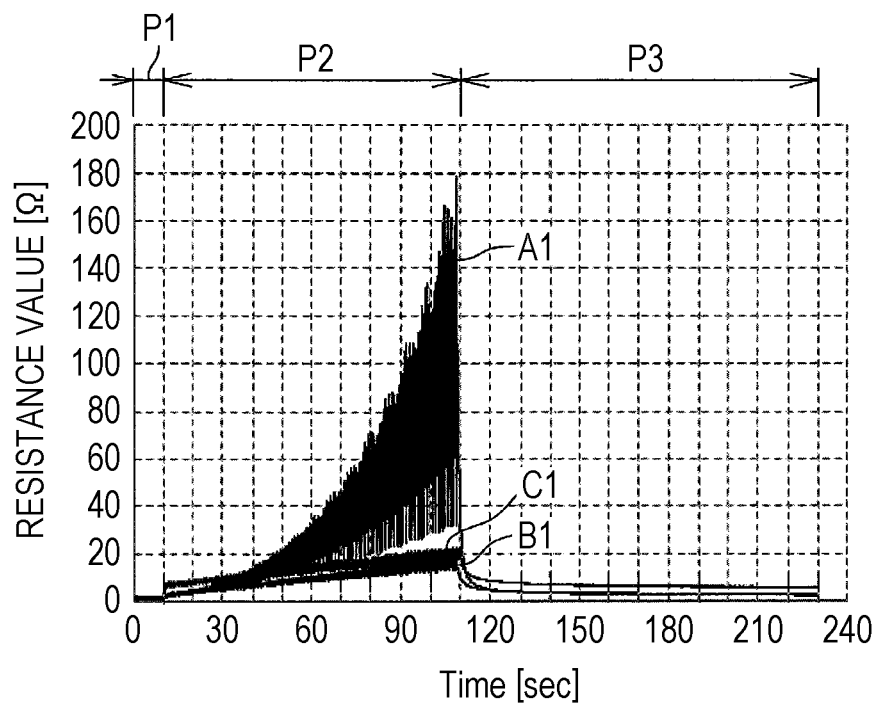
FIG. 3A is a graph illustrating changes in the resistance values of samples a1, b1, and c1 when a 20% tensile strain was applied to mainly the samples a1, b1, and c1 repeatedly 100 times at a frequency of 1.0 Hz.
Figure 3B:
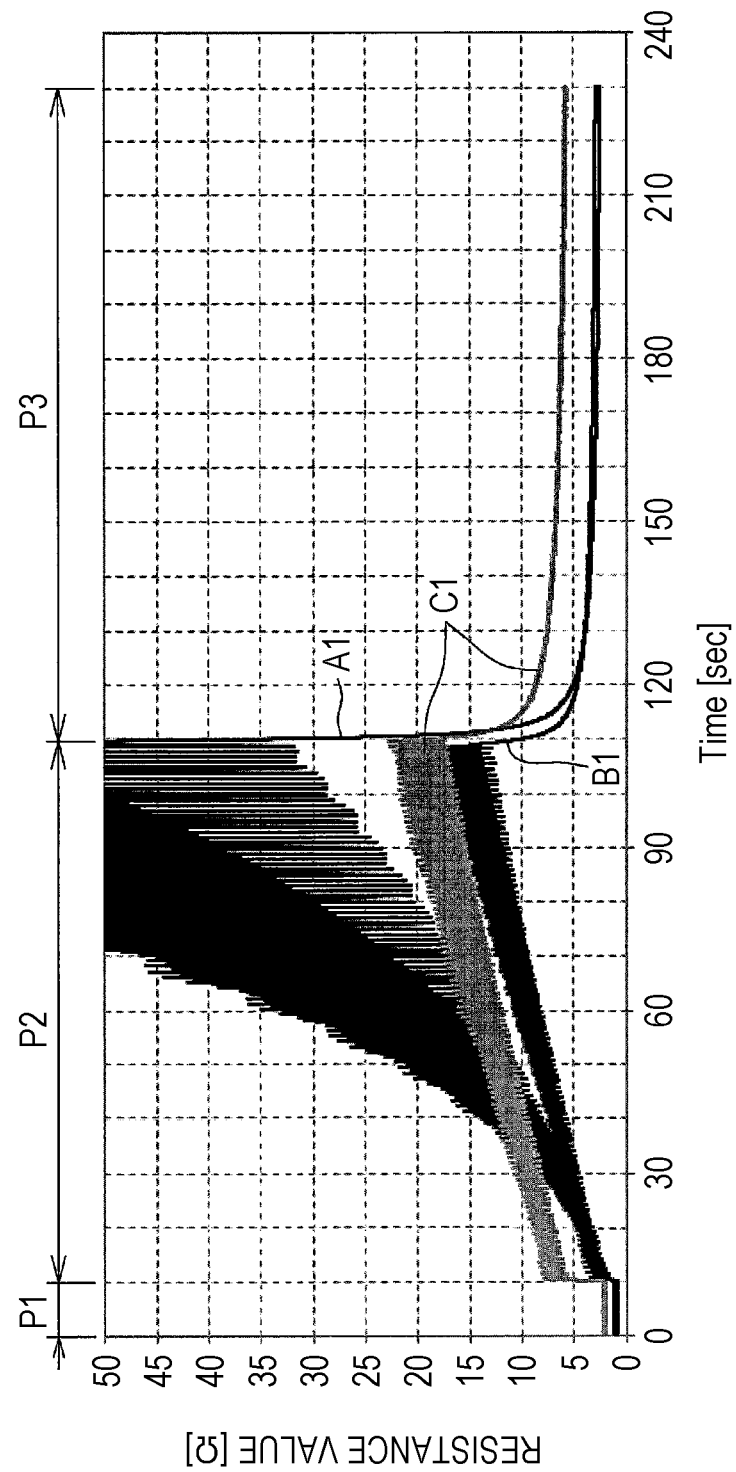
FIG. 3B is a graph, enlarged, of a part of FIG. 3A in a resistance value range of from 0Ω to 50Ω of broken curves A1, B1, and C1.

FIG. 3A, FIG. 3B, and FIG. 3C show graphs illustrating the results of the first evaluation experiment. The broken curves A1, B1, and C1 of FIG. 3A respectively indicate changes in the resistance values of the samples a1, b1, and c1. FIG. 3B shows a part, enlarged, of FIG. 3A in a resistance value range of from 0Ω to 50Ω of the broken curves A1, B1, and C1. The broken curves D1, E1, F1, and G1 of FIG. 3C respectively indicate changes in the resistance values of the samples d1, e1, f1, and g1. The units of scale of the horizontal axis and the vertical axis in FIG. 3C are respectively the same as the units of scale of the horizontal axis and the vertical axis in FIG. 3B. In the graphs of FIG. 3A, FIG. 3B, and FIG. 3C, P1, P2, and P3 respectively indicate the first period P1, the second period P2, and the third period P3.

As will be understood from the graphs of FIG. 3A, FIG. 3B, and FIG. 3C, in the second period P2, the resistance values of samples a1, b1, c1, d1, e1, f1, and g1 became greater as the number of times of application of tensile strain was increased. When the periodic application of tensile strain to the samples a1, b1, c1, d1, e1, f1, and g1 was stopped, the resistance values of samples a1, b1, c1, d1, e1, f1, and g1 rapidly became smaller, and then gradually decreased (see the third period P3).

As will also be understood from the graphs of FIG. 3A, FIG. 3B, and FIG. 3C, in the second period P2, the resistance values of samples a1, b1, c1, d1, e1, f1, and g1 had different rates of increase. For example, as illustrated in FIG. 3A and FIG. 3B, with respect to sample a1, the resistance values at the start point of the second period P2 was 0.8Ω, and the maximum value of resistance in the second period P2 was 178.6Ω. With respect to sample b1, the resistance value at the start point of the second period P2 was 1.2Ω, and the maximum value of resistance immediately before the end of the second period P2 was 17.8Ω. With respect to sample c1, the resistance value at the start point of the second period P2 was 2.0Ω, and the maximum value of resistance of the second period P2 was 22.9Ω.

Thus, when the 20% tensile strain was applied to the samples a1, b1, and c1 repeatedly 100 times at a frequency of 1.0 Hz, the resistance value became 30Ω or more in the case of sample a1, while in the case of sample b1 and sample c1, the resistance values became 30Ω or less. Accordingly, it can be predicted that when the filling factor of the dendritic conductive filler in the conductive composition is not less than 70 mass % and not more than 95 mass %, the increase in resistance value upon application of the 20% tensile strain repeatedly 100 times at a frequency of 1.0 Hz will be reduced. It can also be predicted that when the filling factor of the dendritic conductive filler in the conductive composition is not less than 75 mass % and not more than 90 mass %, the increase in resistance value upon application of the 20% tensile strain repeatedly 100 times at a frequency of 1.0 Hz will be reduced more.

As illustrated in FIG. 3C, with respect to sample d1, the resistance value at the start point of the second period P2 was 1.4Ω, and the maximum value of resistance in the second period P2 was 18.0Ω. With respect to sample e1, the resistance value at the start point of the second period P2 was 5.8Ω, and the maximum value of resistance in the second period P2 was 40.6Ω. With respect to sample f1, the resistance value at the start point of the second period P2 was 0.8Ω, and the maximum value of resistance in the second period P2 was 8.4Ω. With respect to sample g1, the resistance value at the start point of the second period P2 was 1.8Ω, and the maximum value of resistance in the second period P2 was 18.2Ω. This indicates that, for the same thickness of the samples, the samples f1 and g1 using silver powder, compared with the samples d1 and e1 using silver-coated copper powder, have smaller rates of increase in resistance value in the second period P2 and smaller maximum values of resistance in the second period P2. In other words, when the samples have the same length and the same width, in order to make the maximum value of resistance in the second period P2 less than or equal to a predetermined value, the thickness of the stretchable conductive layer can be made thinner in samples f1 and g1 using silver powder than in samples d1 and e1 using silver-coated copper powder.

[Second Evaluation Experiment]

With respect to samples a2, b2, and c2, a second evaluation experiment was conducted. In the second evaluation experiment, first, the samples were maintained in natural state for 10 seconds. This period may be referred to as a first period P1. Then, a 40% tensile strain was applied to the samples repeatedly 100 times at a frequency of 1.0 Hz. This period may be referred to as a second period P2. The second period P2 was 100 seconds. Finally, the samples were again maintained in natural state for 120 seconds. This period may be referred to as a third period P3. During each of these periods, the resistance between the ends of the samples were measured.

Figure 4:
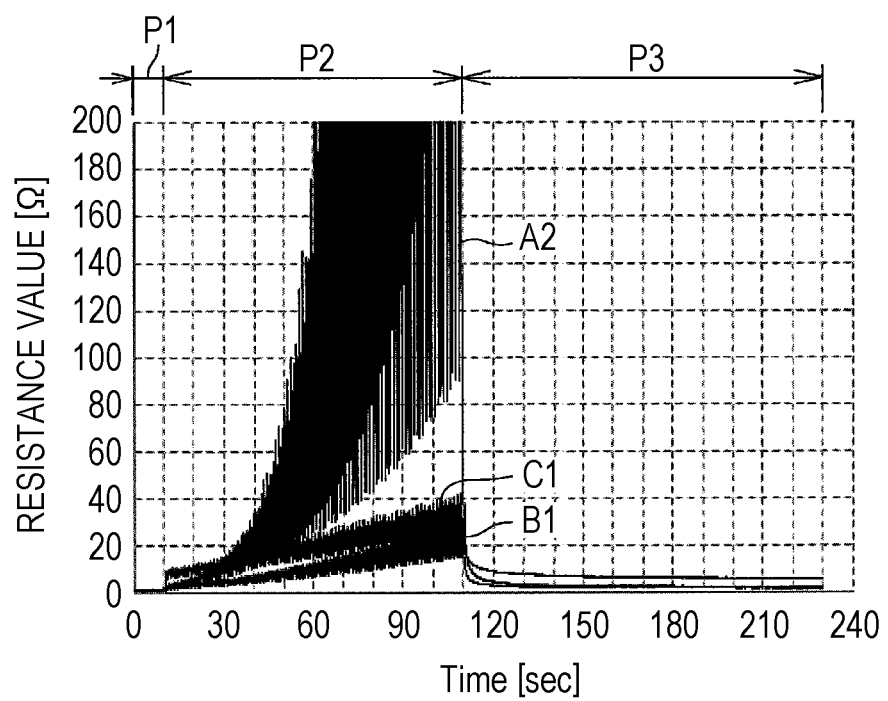
FIG. 4 is a graph illustrating changes in the resistance values of samples a2, b2, and c2 when a 40% tensile strain was applied mainly to the samples a2, b2, and c2 repeatedly 100 times at a frequency of 1.0 Hz.

FIG. 4 is a graph illustrating the results of the second evaluation experiment. In the graph of FIG. 4, broken curves A2, B2, and C2 respectively indicate changes in the resistance values of samples a2, b2, and c2. Further, in the graph of FIG. 4, P1, P2, and P3 respectively indicate the first period P1, the second period P2, and the third period P3. As will be understood from the graph of FIG. 4, in the second period P2, the resistance values of the samples a2, b2, and c2 became greater as the number of times of application of tensile strain was increased. When the periodic application of tensile strain to the samples was stopped, the resistance values of the samples a2, b2, and c2 rapidly became smaller, and then gradually decreased (see the third period P3).

As will be understood from the graph of FIG. 4, in the second period P2, the samples a2, b2, and c2 had different rates of increase in resistance value. Specifically, with respect to sample a2, the resistance value at the start point of the second period P2 was 0.3Ω, and the maximum value of resistance in the second period P2 was 200Ω or more (measurement limit). With respect to sample b2, the resistance value at the start point of the second period P2 was 0.3Ω, and the maximum value of resistance in the second period P2 was 31.4Ω. With respect to sample c2, the resistance value at the start point of the second period P2 was 1.4Ω, and the maximum value of resistance in the second period P2 was 41.9Ω.

That is, when the 40% tensile strain was applied to the samples a2, b2, and c2 repeatedly 100 times at a frequency of 1.0 Hz, the maximum value of resistance was 50Ω or more in the case of sample a2, while the maximum value of resistance was not more than 50Ω in the case of samples b2 and c2. Accordingly, it can be predicted that when the filling factor of the dendritic conductive filler in the conductive composition is not less than 70 wt % and not more than 95 wt %, the increase in resistance value upon application of a 40% tensile strain repeatedly 100 times at a frequency of 1.0 Hz will be decreased. Further, it can be predicted that when the filling factor of the dendritic conductive filler in the conductive composition is not less than 75 mass % and not more than 90 mass %, the increase in resistance value upon application of a 40% tensile strain repeatedly 100 times at a frequency of 1.0 Hz will be reduced more.

[Third Evaluation Experiment]

With respect to the samples a3, b3, c3, d3, e3, f3, and g3, a third evaluation experiment was conducted. The third evaluation experiment was conducted as follows. First, the resistance value between the ends of the samples before elongation was measured. Thereafter, the samples were elongated to a plurality of predetermined lengths, and the resistance value between the ends of the samples after elongation was measured. The measurement of the resistance value was performed in an elongation rate range of from 0% to 200% with respect to a plurality of kinds of elongation rates varying at 20% intervals.

Table 2 shows the results of the third evaluation experiment with respect to sample a3. Table 3 shows the results of the third evaluation experiment with respect to sample b3. Table 4 shows the results of the third evaluation experiment with respect to sample c3. Table 5 shows the results of the third evaluation experiment with respect to sample d3. Table 6 shows the results of the third evaluation experiment with respect to sample e3. Table 7 shows the results of the third evaluation experiment with respect to sample f3. Table 8 shows the results of the third evaluation experiment with respect to sample g3.

Figure 5B:
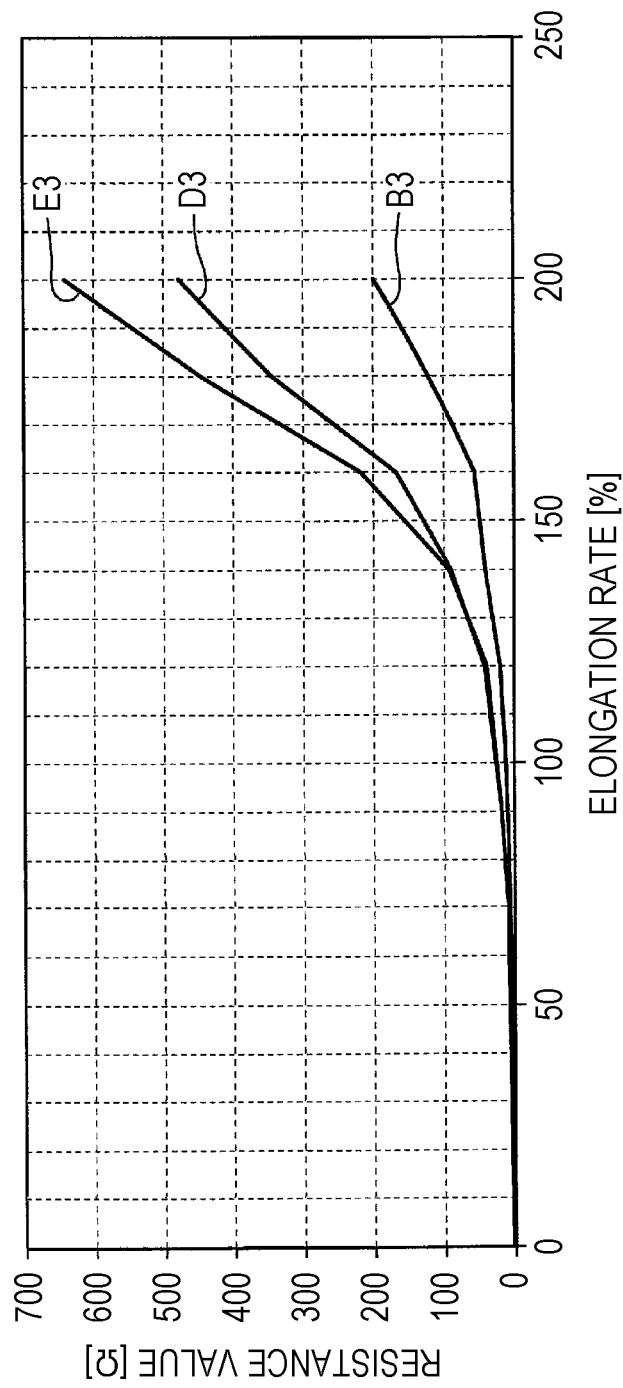
FIG. 5B is a graph only relating to the samples b3, d3, and e3 extracted from the graph shown in FIG. 5A.
Figure 5C:
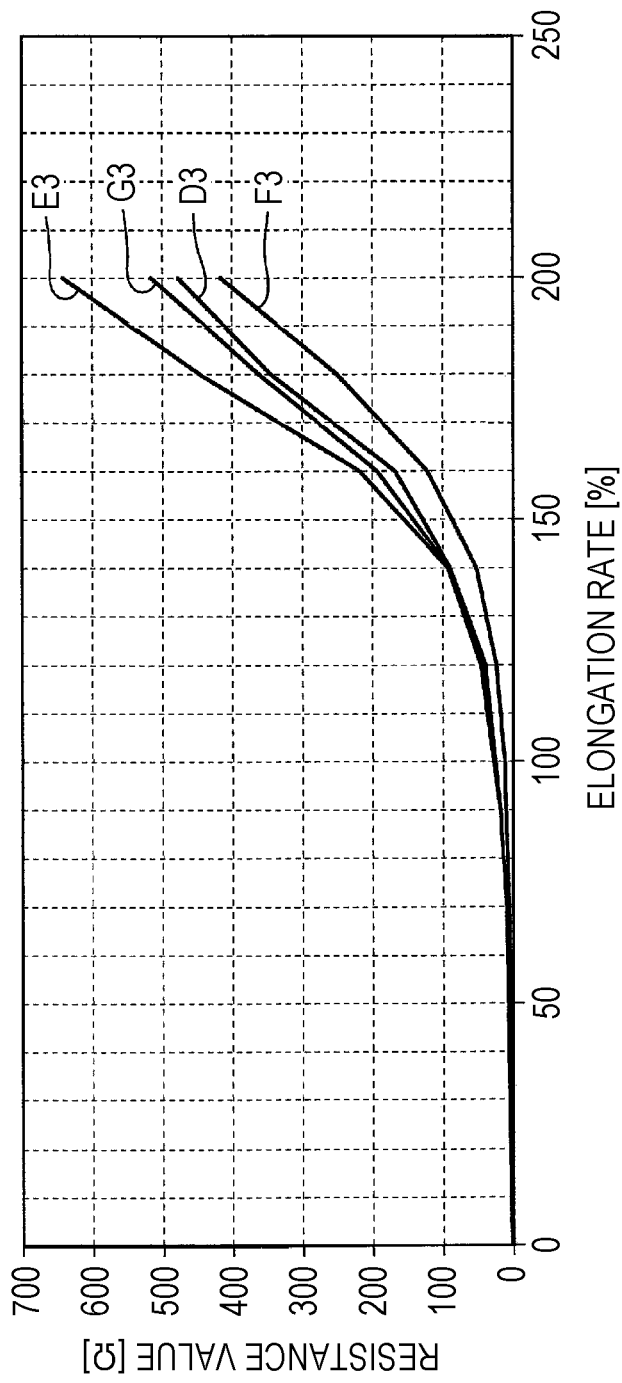
FIG. 5C is a graph only relating to the samples d3, e3, f3, and g3 extracted from the graph shown in FIG. 5A.

FIG. 5A, FIG. 5B, and FIG. 5C are graphs illustrating the results of the third evaluation experiment. In the graph of FIG. 5A, broken curves A3, B3, C3, D3, E3, F3, and G3 respectively indicate the resistance values relative to elongation rate of the samples a3, b3, c3, d3, e3, f3, and g3. FIG. 5B is a graph only illustrating B3, D3, and E3 among the broken curves A3 to G3 in FIG. 5A. FIG. 5C is a graph only illustrating D3, E3, F3, and G3 among the broken curves A3 to G3 in FIG. 5A.

TABLE 2

Sample a3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.257 | 0.257 |
| 5 | 6 | 20 | 0.238 | 0.682 |
| 5 | 7 | 40 | 0.228 | 2.424 |
| 5 | 8 | 60 | 0.254 | 5.787 |
| 5 | 9 | 80 | 0.265 | 11.523 |
| 5 | 10 | 100 | 0.270 | 29.093 |
| 5 | 11 | 120 | 0.272 | 38.240 |
| 5 | 12 | 140 | 0.267 | 204.820 |
| 5 | 13 | 160 | 0.263 | Non-conducting |
| 5 | 14 | 180 | — | — |
| 5 | 15 | 200 | — | — |

TABLE 3

Sample b3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.173 | 0.173 |
| 5 | 6 | 20 | 0.182 | 0.733 |
| 5 | 7 | 40 | 0.176 | 1.892 |
| 5 | 8 | 60 | 0.169 | 3.472 |
| 5 | 9 | 80 | 0.176 | 6.993 |
| 5 | 10 | 100 | 0.171 | 12.947 |
| 5 | 11 | 120 | 0.171 | 18.853 |
| 5 | 12 | 140 | 0.173 | 39.920 |
| 5 | 13 | 160 | 0.175 | 57.840 |
| 5 | 14 | 180 | 0.172 | 123.910 |
| 5 | 15 | 200 | 0.162 | 203.120 |

TABLE 4

Sample c3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.790 | 0.790 |
| 5 | 6 | 20 | 0.765 | 2.557 |
| 5 | 7 | 40 | 0.869 | 5.299 |
| 5 | 8 | 60 | 0.773 | 9.226 |
| 5 | 9 | 80 | 0.909 | 17.094 |
| 5 | 10 | 100 | 0.816 | 27.195 |
| 5 | 11 | 120 | 0.669 | 46.580 |
| 5 | 12 | 140 | 0.726 | Severed |

TABLE 4-continued

Sample c3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 13 | 160 | — | — |
| 5 | 14 | 180 | — | — |
| 5 | 15 | 200 | — | — |

TABLE 5

Sample d3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.210 | 0.210 |
| 5 | 6 | 20 | 0.285 | 0.860 |
| 5 | 7 | 40 | 0.272 | 2.060 |
| 5 | 8 | 60 | 0.234 | 4.001 |
| 5 | 9 | 80 | 0.257 | 11.800 |
| 5 | 10 | 100 | 0.289 | 22.780 |
| 5 | 11 | 120 | 0.212 | 48.130 |
| 5 | 12 | 140 | 0.279 | 93.190 |
| 5 | 13 | 160 | 0.268 | 169.270 |
| 5 | 14 | 180 | 0.274 | 343.700 |
| 5 | 15 | 200 | 0.220 | 480.600 |

TABLE 6

Sample e3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.305 | 0.305 |
| 5 | 6 | 20 | 0.297 | 1.254 |
| 5 | 7 | 40 | 0.299 | 3.472 |
| 5 | 8 | 60 | 0.279 | 6.602 |
| 5 | 9 | 80 | 0.296 | 13.665 |
| 5 | 10 | 100 | 0.301 | 23.085 |
| 5 | 11 | 120 | 0.303 | 44.030 |
| 5 | 12 | 140 | 0.340 | 92.820 |
| 5 | 13 | 160 | 0.322 | 218.720 |
| 5 | 14 | 180 | 0.316 | 448.800 |
| 5 | 15 | 200 | 0.296 | 640.500 |

TABLE 7

Sample f3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.135 | 0.135 |
| 5 | 6 | 20 | 0.165 | 0.572 |
| 5 | 7 | 40 | 0.127 | 1.940 |
| 5 | 8 | 60 | 0.122 | 3.820 |
| 5 | 9 | 80 | 0.148 | 7.780 |
| 5 | 10 | 100 | 0.139 | 12.960 |
| 5 | 11 | 120 | 0.155 | 25.120 |
| 5 | 12 | 140 | 0.144 | 51.870 |
| 5 | 13 | 160 | 0.139 | 122.140 |
| 5 | 14 | 180 | 0.151 | 250.300 |
| 5 | 15 | 200 | 0.120 | 420.400 |

TABLE 8

Sample g3

| Before elongation Length L1 (cm) | After elongation Length L2 (cm) | After elongation Elongation rate r (%) | Before elongation Resistance value R1 (Ω) | After elongation Resistance value R2 (Ω) |
|---|---|---|---|---|
| 5 | 5 | 0 | 0.213 | 0.213 |
| 5 | 6 | 20 | 0.228 | 1.267 |
| 5 | 7 | 40 | 0.251 | 3.380 |
| 5 | 8 | 60 | 0.233 | 6.509 |
| 5 | 9 | 80 | 0.239 | 9.200 |
| 5 | 10 | 100 | 0.222 | 21.710 |
| 5 | 11 | 120 | 0.246 | 38.550 |
| 5 | 12 | 140 | 0.237 | 90.800 |
| 5 | 13 | 160 | 0.221 | 196.200 |
| 5 | 14 | 180 | 0.256 | 361.500 |
| 5 | 15 | 200 | 0.249 | 520.100 |

In Table 2 to Table 8, the length L1 indicates the lengths of the samples before elongation. The length L1 of the samples a3, b3, c3, d3, e3, f3, and g3 before elongation was 5 cm. The length L2 indicates the lengths of the samples after elongation. The stretch rate r is the values computed based on the expression (1). The resistance value R1 indicates the resistance values of the samples before elongation. The resistance value R2 indicates the resistance values of the samples after elongation.

As illustrated in FIG. 5A, FIG. 5B, and FIG. 5C, in all of the samples a3, b3, c3, d3, e3, f3, and g3, the resistance value R2 when stretched at the stretch rate of 120% was not more than 50Ω. In this way, it will be seen that the conductive compositions according to Examples 1 to 7 are stretchable and able to suppress an increase in resistivity when stretched. In addition, as illustrated in FIG. 5A, the sample c3 became severed when stretched at the stretch rate of 140%, resulting in a non-conducting state (see also Table 4). The sample a3, when stretched at the stretch rate of 160%, did not become severed but resulted in a non-conducting state (see also Table 2). On the other hand, the samples b3, d3, e3, f3, and g3, as illustrated in FIG. 5A, FIG. 5B, and FIG. 5C, did not result in a non-conducting state even when stretched at the stretch rate of 200%. The resistance value R2 of the samples b3, d3, e3, f3, and g3 when stretched at the stretch rate of 200% was 203Ω, 481Ω, 641Ω, 420Ω, and 520Ω, respectively (see also Table 3 to Table 8).

Thus, it can be predicted that when the filling factor of the conductive filler in the conductive composition is not less than 70 mass % and not more than 95 mass %, the stretch properties will be enhanced and it will become possible to suppress an increase in resistance value upon elongation. Also, it can be predicted that when the filling factor of the conductive filler in the conductive composition is not less than 75 mass % and not more than 90 mass %, the stretch properties will be more enhanced and it will become possible to suppress an increase in resistance value upon elongation even more. Further, it can be predicted that when the filling factor of the conductive filler in the conductive composition is not less than 75 mass % and not more than 85 mass %, the stretch properties will become extremely high and it will become possible to more effectively suppress an increase in resistance value upon elongation.

It is also seen from FIG. 5B that the smaller the thickness of the samples, the higher the resistance value R2 becomes when stretched at the stretch rate of 200%. It is also seen that, from a comparison of the broken curves D3 and F3 and a comparison of the broken curves E3 and G3 in FIG. 5C, when the thicknesses of the samples are the same, the resistance value R2 when stretched at the stretch rate of 200% becomes lower if a silver powder is used as the conductive filler than if a silver-coated copper powder is used.

In the foregoing Examples 1 to 7, as the elastomer, PANDEX 372E manufactured by DIC corporation or NE-310 manufactured by Dainichiseika Color & Chemicals Mfg. Co., Ltd. was used. As the elastomer, NE-8880, MAU-9022, NE-302HV, CU-8448 and the like manufactured by Dainichiseika Color & Chemicals Mfg. Co., Ltd may also be used.

[Method for Manufacturing Stretchable Conductive Film for Textiles]

Figure 6A:
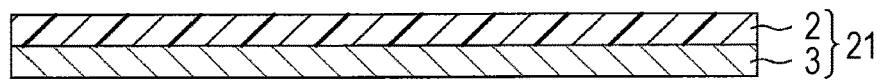
FIG. 6A to FIG. 6C are process diagrams illustrating a method for manufacturing a stretchable conductive film.
Figure 6B:
Figure 6C:
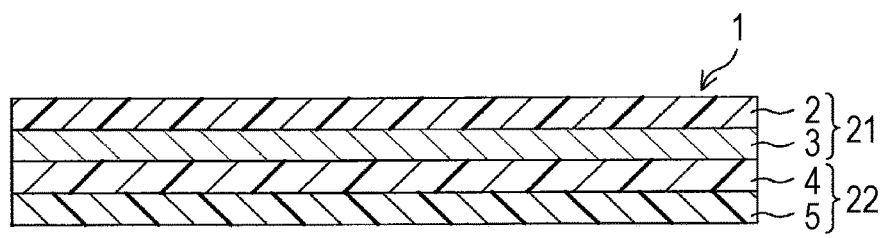

FIG. 6A to FIG. 6C are process diagrams illustrating a method for manufacturing the stretchable conductive film 1.

First, as illustrated in FIG. 6A, the stretchable conductive layer 3 is formed on one surface of the first peel film 2, fabricating a first laminated film 21.

Then, as illustrated in FIG. 6B, the hot-melt adhesive agent layer 4 is formed on one surface of the second peel film 5, fabricating a second laminated film 22.

Finally, as illustrated in FIG. 6C, the surface of the first laminated film 21 on the side of the stretchable conductive layer 3 and the surface of the second laminated film 22 on the side of the hot-melt adhesive agent layer 4 are laminate-adhered to each other. In this way, the stretchable conductive film 1 is obtained.

Figure 7A:
FIG. 7A to FIG. 7C are process diagrams illustrating another method for manufacturing a stretchable conductive film.
Figure 7B:
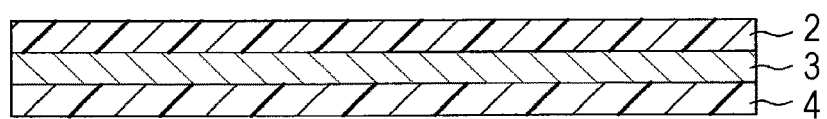
Figure 7C:
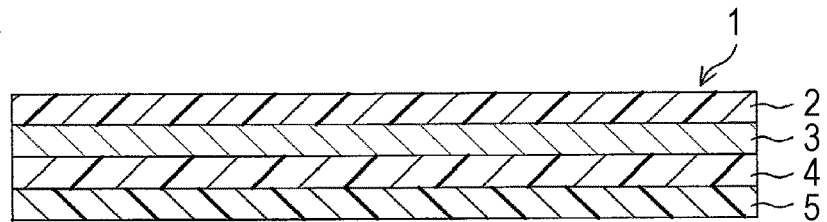

FIG. 7A to FIG. 7C are process diagrams illustrating another method for manufacturing the stretchable conductive film 1.

First, as illustrated in FIG. 7A, the stretchable conductive layer 3 is formed on one surface of the first peel film 2.

Then, as illustrated in FIG. 7B, the hot-melt adhesive agent layer 4 is formed on the surface of the stretchable conductive layer 3 on the opposite side from the first peel film 2 side.

Finally, as illustrated in FIG. 7C, the second peel film 5 is attached to the surface of the hot-melt adhesive agent layer 4 on the opposite side from the stretchable conductive layer 3 side. In this way, the stretchable conductive film 1 is obtained.

[Method for Using the Stretchable Conductive Film for Textiles]

With reference to FIG. 8A to FIG. 8D, a method for using the stretchable conductive film 1 will be described.

First, the stretchable conductive film 1 is cut to a shape in accordance with the purpose of use.

Figure 8A:
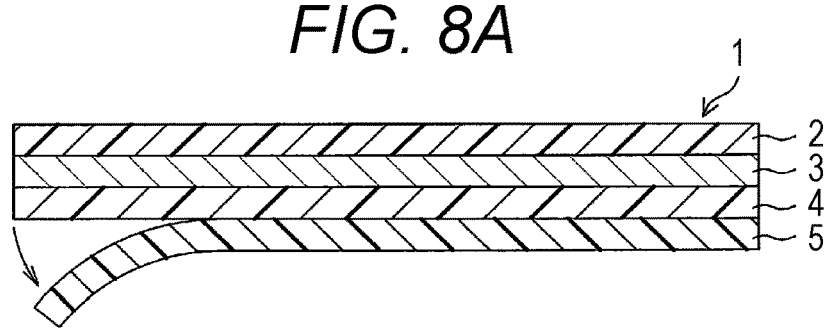
FIG. 8A to FIG. 8D are schematic cross sectional views for describing a method for using a stretchable conductive film.

Then, as illustrated in FIG. 8A, the second peel film 5 is peeled from the stretchable conductive film 1.

Figure 8B:
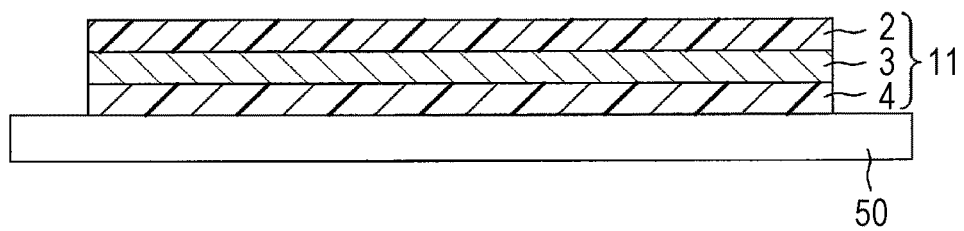

Thereafter, as illustrated in FIG. 8B, the stretchable conductive film 1 from which the second peel film 5 has been peeled (which may be hereinafter referred to as "stretchable conductive film 11") is placed on a textile fabric 50 in such a way that the surface of the stretchable conductive film 1 on the side of the hot-melt adhesive agent layer 4 opposes the textile fabric 50. Then, an iron or the like is used to thermally bond the stretchable conductive film 11 onto the textile fabric 50.

Figure 8C:
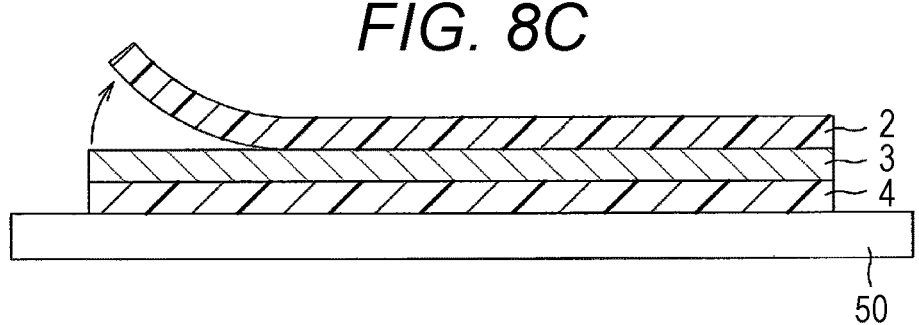
Figure 8D:
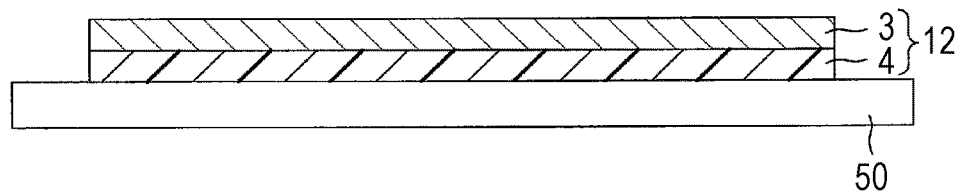

Thereafter, as illustrated in FIG. 8C, the first peel film 2 is peeled from the stretchable conductive film 11. In this way, as illustrated in FIG. 8D, the stretchable conductive film 1 comprising the stretchable conductive layer 3 and the hot-melt adhesive agent layer 4 (which may be hereinafter referred to as "stretchable conductive film 12") is placed in a state of being attached to the textile fabric 50.

[Mode of Use of the Stretchable Conductive Film for Textiles]

The stretchable conductive film 1 is used as an electrode and wiring material for biometric information measurement, such as electrocardiographic measurement and myoelectric measurement.

Figure 9:
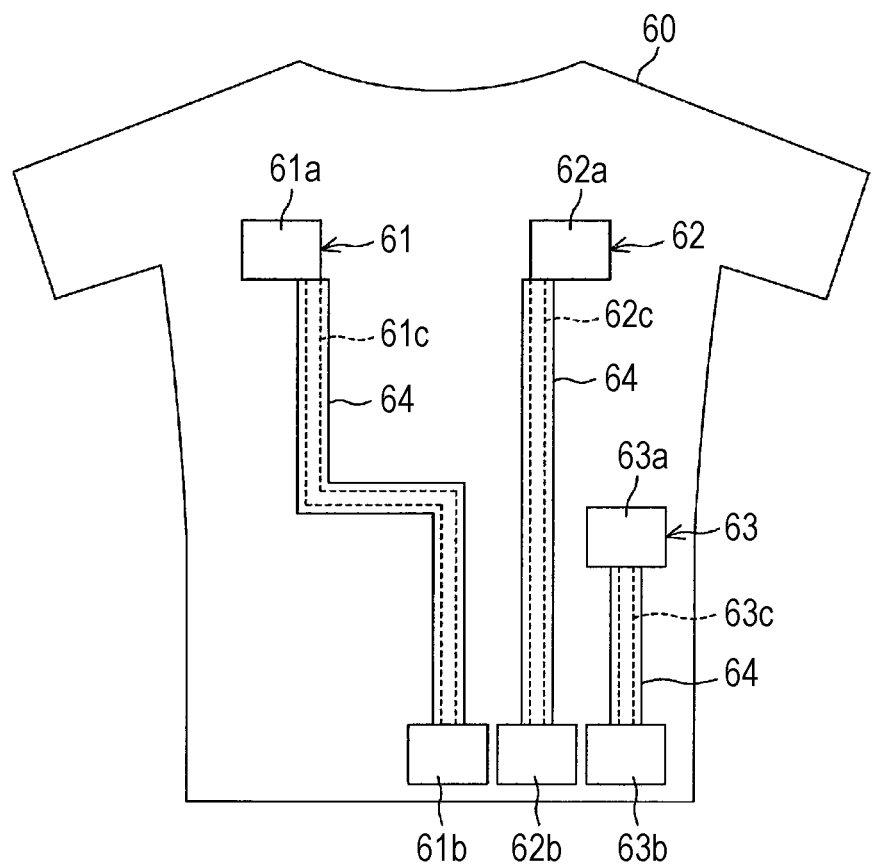
FIG. 9 is a schematic diagram illustrating an example in which a stretchable conductive film is used as an electrode and wiring material for electrocardiographic measurement.

FIG. 9 is a schematic diagram illustrating an example in which the stretchable conductive film 1 is used as an electrode and wiring material for electrocardiographic measurement.

A shirt 60 made of a stretchy fabric has an electrocardiographic measurement wiring pattern configured from the stretchable conductive film 12 attached to the back surface of the front side thereof. The electrocardiographic measurement wiring pattern includes a first wiring 61, a second wiring 62, and a third wiring 63. The wiring 61, 62, and 63 respectively include electrode portions 61a, 62a, and 63a; terminal portions 61b, 62b, and 63b; and wiring portions 61c, 62c, and 63c connecting the electrode and terminal portions. The electrode portions 61a, 62a, and 63a are the portions that contact the human body, and constitute electrocardiographic measurement electrodes. The electrode portions 61a and 62a of the first wiring 61 and second wiring 62 are disposed in positions corresponding to the chest on the back surface of the front side of the shirt 60. The electrode portion 63a of the third wiring 63 is disposed in a position corresponding to the flank on the back surface of the front side of the shirt 60. The terminal portions 61b, 62b, and 63b constitute terminals for connecting the wiring 61, 62, and 63 to an electrocardiograph. The terminal portions 61b, 62b, and 63b are disposed at the lower end on the back surface of the front side of the shirt 60.

To the back surface of the front side of the shirt 60, elongated stretchable protection films 64 are attached, the films covering the wiring portions 61c, 62c, and 63c of the respective wiring 61, 62, and 63. The stretchable protection films 64 serve to insulate the surfaces (stretchable conductive layer 3) of the wiring portions 61c, 62c, and 63c, and to prevent the development of scratches (damage) on the surfaces (stretchable conductive layer 3) of the wiring portions 61c, 62c, and 63c. As the foregoing stretchable protection films 64, the elastomer used in the stretchable conductive layer 3 that is filled with carbon black, for example, may be used. The stretchable protection films 64 may similarly include additives such as a plasticizer, a processing aid, a cross-linker, a vulcanization accelerator, a vulcanization aid, an anti-oxidant, a softener, and a coloring agent.

Figure 10:
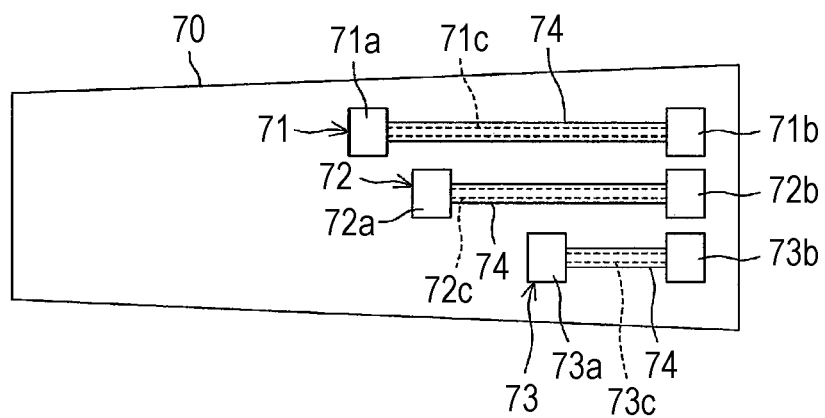
FIG. 10 is a schematic diagram illustrating an example in which a stretchable conductive film is used as an electrode and wiring material for electromyographic measurement.

FIG. 10 is a schematic diagram illustrating an example in which the stretchable conductive film 1 is used as an electrode and wiring material for electromyographic measurement.

To the back surface (inner peripheral surface) of an arm cover 70 worn on the forearm, a wiring pattern for electromyographic measurement configured from the stretchable conductive film 12 is attached. The arm cover 70 is made of a stretchy fabric. The wiring pattern for electromyographic measurement includes a first wiring 71, a second wiring 72, and a third wiring 73. The wiring 71, 72, and 73 respectively include electrode portions 71a, 72a, and 73a; terminal portions 71b, 72b, and 73b; and wiring portions 71c, 72c, and 73c connecting the electrode and terminal portions. The electrode portions 71a, 72a, and 73a are the portions that contact the human body, and constitute electromyographic measurement electrodes. The electrode portions 71a, 72a, and 73a are disposed in positions corresponding to the forearm muscle portion on the back surface of the arm cover 70. The terminal portions 71b, 72b, and 73b constitute terminals for connecting the wiring 71, 72, and 73 to the electromyograph. The terminal portions 71b, 72b, and 73b are disposed at one end of the arm cover 70.

To the back surface of the arm cover 70, elongated stretchable protection films 74 are attached, the films covering the wiring portions 71c, 72c, and 73c of the respective wiring 71, 72, and 73. The stretchable protection films 74 are made from the same material as the stretchable protection films 64.

[Evaluation Test for Stretchable Conductive Film]

A plurality of kinds of samples of the stretchable conductive film 1 was fabricated. The samples were attached to a stretchy fiber fabric by the method described with reference to FIG. 8A to FIG. 8D. In this way, a plurality of kinds of test samples h, i, and j was fabricated. The stretchable conductive film 1 was attached to the stretchy fiber fabric by thermal bonding using an iron at 120° C. The test samples h, i, and j were subjected to an evaluation test. The content and evaluation results of the evaluation test will be described.

Figure 11A:
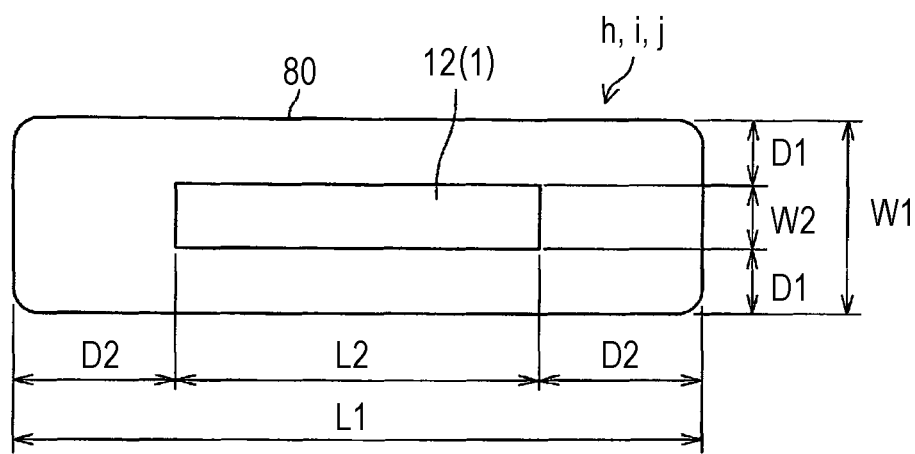
FIG. 11A is a plan view diagrammatically illustrating a configuration of a test sample.
Figure 11B:
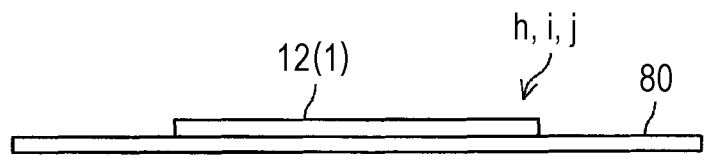
FIG. 11B is a front view diagrammatically illustrating the configuration of the test sample.

FIG. 11A is a plan view diagrammatically illustrating the configuration of the test samples. FIG. 11B is a front view diagrammatically illustrating the configuration of the test samples.

Each of the test samples h, i, and j included a stretchy fiber fabric 80 which was rectangular as viewed in plan, and a stretchable conductive film 12(1). The stretchable conductive film 12(1) was attached to a surface central portion of the stretchy fiber fabric 80, and was rectangular as viewed in plan. The stretchable conductive film 12 attached to the stretchy fiber fabric 80 included the hot-melt adhesive agent layer 4 on the stretchy fiber fabric 80 side, and the stretchable conductive layer 3 formed on the hot-melt adhesive agent layer 4.

In the test samples h, i, and j, the stretchy fiber fabric 80 had the same shape, size, material and the like. The stretchy fiber fabric 80 had a length L1 of 100 mm and a width W1 of 30 mm. The stretchy fiber fabric 80 had a thickness of 0.37 mm.

The test samples h, i, and j had the same planar shape and size of the stretchable conductive film 12. The stretchable conductive film 12 had a length L2 of 50 mm and a width W2 of 10 mm. As viewed in plan, an interval D1 between the long sides of the stretchy fiber fabric 80 and the corresponding long sides of the stretchable conductive film 12 was 10 mm. An interval D2 between the short sides of the stretchy fiber fabric 80 and the corresponding short sides of the stretchable conductive film 12 was 25 mm.

In the test samples h, i, and j, the conductive composition of the stretchable conductive layer 3 had the same material and thickness. Specifically, the conductive filler was a dendritic silver-coated copper powder with an average grain size of 5 μm (manufactured by MITSUI MINING & SMELTING CO., LTD.). The filling factor of the silver-coated copper powder (filling factor of the conductive filler in the conductive composition) was 80 mass %. The elastomer was a polyurethane-based elastomer (NE-310 manufactured by Dainichiseika Color & Chemicals Mfg. Co., Ltd.). The stretchable conductive layer 3 had a thickness of 60 μm.

In the test samples h, i, and j, the material of the hot-melt adhesive agent layer 4 was the same. However, the hot-melt adhesive agent layer 4 had different thicknesses. The hot-melt adhesive agent layer 4 was a thermoplastic polyurethane (SHM101-PUR manufactured by Sheedom Co., Ltd., melting point 115° C., durometer hardness 75 A, and rupture elongation 800%). The test sample h had a thickness of 30 μm. The test sample i had a thickness of 70 μm. The test sample j had a thickness of 100 μm.

Three each of the test samples h, i, and j were fabricated. The test samples were individually subjected to the evaluation test. During the evaluation test, one end of the test sample was fixed, and the other end was pulled at a constant speed (200 mm/sec in the present example). At constant time intervals, the stretch rate (%) of the test sample and the resistance value (Ω) between the ends of the stretchable conductive film 12 were measured. The central value of the time-based resistance values of the three test samples h was considered as the time-based resistance value of the test sample h. The central value of the time-based resistance values of the three test samples i was considered as the time-based resistance value of the test sample i. The central value of the time-based resistance values of the three test samples j was considered as the time-based resistance value of the test sample j.

Figure 12:
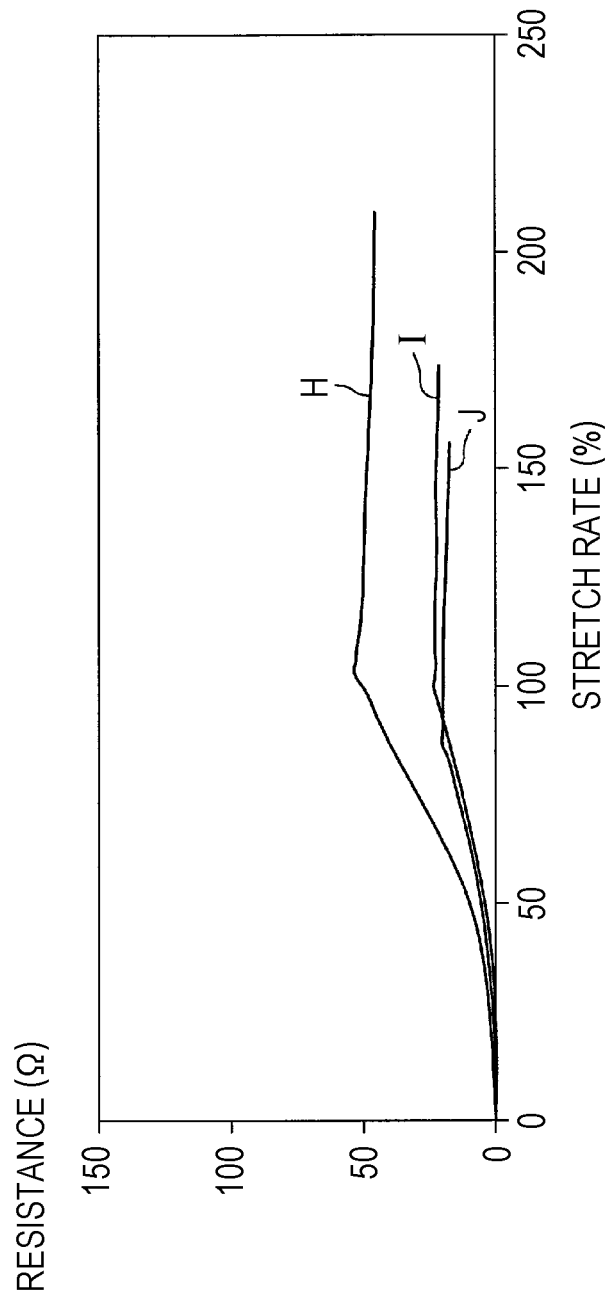
FIG. 12 is a graph illustrating the results of an evaluation test with respect to test samples.

FIG. 12 is a graph illustrating the results of the evaluation test with respect to the test samples. In FIG. 12, the curved lines H, I, and J indicate changes in the resistance values of the test samples h, i, and j.

It will be seen from the graph that as the thickness of the hot-melt adhesive agent layer 4 increased, the maximum stretch rate of the stretchable conductive film 12 became smaller and the resistance value relative to the stretch rate of the stretchable conductive film 12 became smaller.

While an embodiment of the present invention has been described, the present invention may be implemented in other embodiments. In the foregoing embodiment, the stretchable conductive film 1 includes the first peel film 2, the stretchable conductive layer 3, the hot-melt adhesive agent layer 4, and the second peel film 5. The stretchable conductive film, however, may have a structure different from that of the foregoing embodiment as long as the stretchable conductive layer and the hot-melt adhesive agent layer formed on one surface of the stretchable conductive layer are included.

In the following, the configurations of the stretchable conductive film according to the second to sixth embodiments of the present invention will be described with reference to FIG. 13A to FIG. 13E.

Figure 13A:
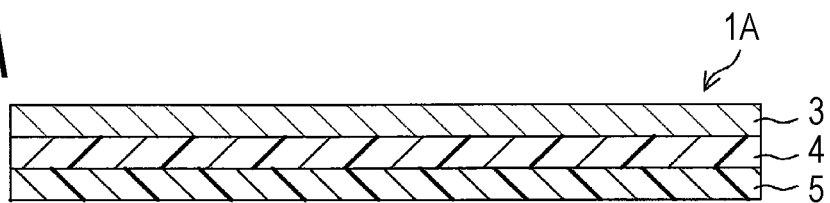
FIG. 13A to FIG. 13E are respectively cross sectional views illustrating the configuration of stretchable conductive films according to the second to sixth embodiments.

FIG. 13A is a cross sectional view illustrating the configuration of the stretchable conductive film according to a second embodiment of the present invention. The stretchable conductive film 1A includes the stretchable conductive layer 3, the hot-melt adhesive agent layer 4, and the peel film 5. The hot-melt adhesive agent layer 4 is formed on one surface of the stretchable conductive layer 3. The peel film 5 is formed on the surface of the hot-melt adhesive agent layer 4 on the opposite side from the stretchable conductive layer 3 side.

Figure 13B:
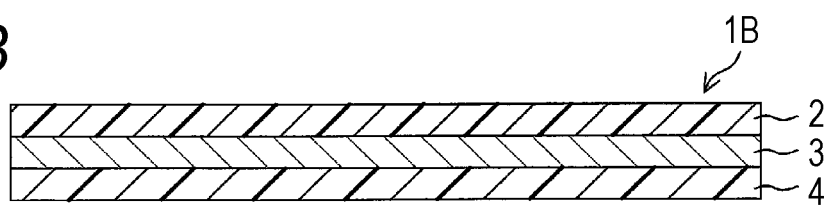

FIG. 13B is a cross sectional view illustrating the configuration of the stretchable conductive film according to a third embodiment of the present invention. The stretchable conductive film 1B includes the stretchable conductive layer 3, the hot-melt adhesive agent layer 4, and the peel film 2. The hot-melt adhesive agent layer 4 is formed on one surface of the stretchable conductive layer 3. The peel film 2 is formed on the surface of the stretchable conductive layer 3 on the opposite side from the hot-melt adhesive agent layer 4 side.

Figure 13C:
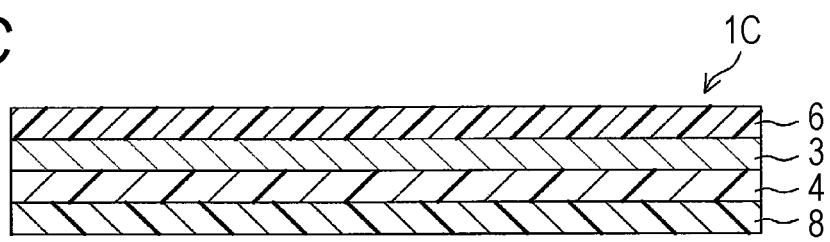

FIG. 13C is a cross sectional view illustrating the configuration of the stretchable conductive film according to a fourth embodiment of the present invention. The stretchable conductive film 1C includes the stretchable conductive layer 3, the hot-melt adhesive agent layer 4, a stretchable protection layer 6, and a peel film 8. The hot-melt adhesive agent layer 4 is formed on one surface of the stretchable conductive layer 3. The stretchable protection layer 6 is formed in at least a part on the surface of the stretchable conductive layer 3 on the opposite side from the hot-melt adhesive agent layer 4 side. The peel film 8 is formed on the surface of hot-melt adhesive agent layer 4 on the opposite side from the stretchable conductive layer 3 side. The stretchable protection layer 6 serves to insulate a part or all of the surface of the stretchable conductive layer 3 on the opposite side from the hot-melt adhesive agent layer 4 side. The stretchable protection layer 6 also serves to prevent the development of scratches (damage) in a part or all of the surface of the stretchable conductive layer 3 on the opposite side from the hot-melt adhesive agent layer 4 side. As the stretchable protection layer 6, the elastomer used in the stretchable conductive layer 3 that is filled with carbon black, for example, may be used. The stretchable protection layer 6 may similarly include an additive such as a plasticizer, a processing aid, a cross-linker, a vulcanization accelerator, a vulcanization aid, an anti-oxidant, a softener, and a coloring agent.

Figure 13D:
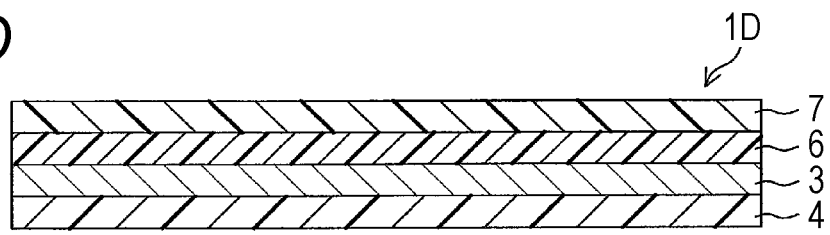

FIG. 13D is a cross sectional view illustrating the configuration of the stretchable conductive film according to a fifth embodiment of the present invention. The stretchable conductive film 1D includes the stretchable conductive layer 3, the hot-melt adhesive agent layer 4, the stretchable protection layer 6, and a peel film 7. The hot-melt adhesive agent layer 4 is formed on one surface of the stretchable conductive layer 3. The stretchable protection layer 6 is formed in at least a part of the surface of the stretchable conductive layer 3 on the opposite side from the hot-melt adhesive agent layer 4 side. The peel film 7 is formed on the surface of the stretchable conductive layer 3 on the opposite side from the hot-melt adhesive agent layer 4 side so as to cover the stretchable protection layer 6.

Figure 13E:
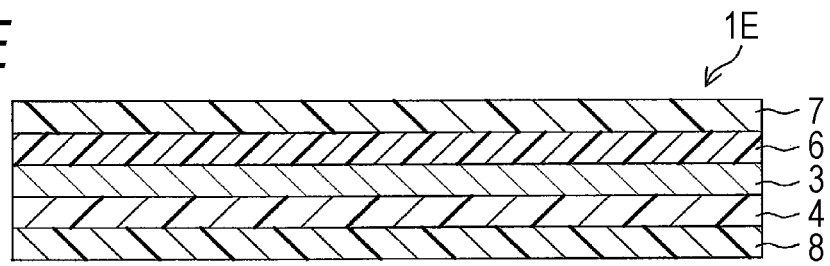

FIG. 13E is a cross sectional view illustrating the configuration of the stretchable conductive film according to a sixth embodiment of the present invention. The stretchable conductive film 1E comprises the stretchable conductive layer 3, the hot-melt adhesive agent layer 4, the stretchable protection layer 6, a first peel film 7, and a second peel film 8. The hot-melt adhesive agent layer 4 is formed on one surface of the stretchable conductive layer 3. The stretchable protection layer 6 is formed in at least a part of the surface of the stretchable conductive layer 3 on the opposite side from the hot-melt adhesive agent layer 4 side. The first peel film 7 is formed on the surface of the stretchable conductive layer 3 on the opposite side from the hot-melt adhesive agent layer 4 side so as to cover the stretchable protection layer 6. The second peel film 8 is formed on the surface of the hot-melt adhesive agent layer 4 on the opposite side from the stretchable conductive layer 3 side.

Figure 14A:
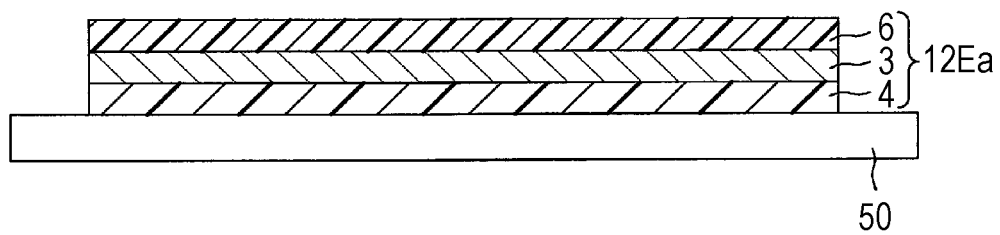
FIG. 14A is a cross sectional view illustrating a use state of the stretchable conductive film according to the sixth embodiment.

FIG. 14A is a cross sectional view illustrating a use state of the stretchable conductive film 1E.

When the stretchable conductive film 1E is used, first, the stretchable conductive film 1E is cut to a shape in accordance with the purpose of use. Then, the second peel film 8 is peeled from the stretchable conductive film 1E. Thereafter, the stretchable conductive film 1E from which the second peel film 8 has been peeled is placed on the textile fabric 50 in such a way that the surface of the stretchable conductive film on the side of the hot-melt adhesive agent layer 4 opposes the textile fabric 50. Then, an iron or the like is used to thermally bond the stretchable conductive film 1E onto the textile fabric 50. Thereafter, the first peel film 7 is peeled from the stretchable conductive film 1E. In this way, as illustrated in FIG. 14A, the stretchable conductive film 1E (indicated by the sign 12Ea in FIG. 14A) including the stretchable protection layer 6, the stretchable conductive layer 3, and the hot-melt adhesive agent layer 4 is placed in a state of being attached to the textile fabric 50.

Figure 14B:
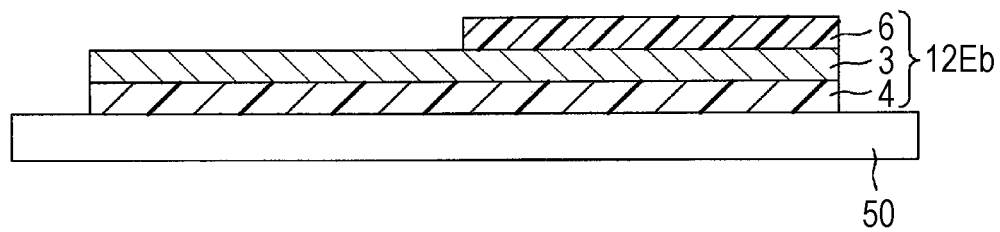
FIG. 14B is a cross sectional view illustrating another example of the use state of the stretchable conductive film according to the sixth embodiment.

FIG. 14B is a cross sectional view illustrating a use state of the stretchable conductive film 1E. In this state, the stretchable protection layer 6 is formed in only a part of the surface of the stretchable conductive layer 3. When the stretchable protection layer 6 is formed in only a part of the surface of the stretchable conductive layer 3, as illustrated in FIG. 14B, the stretchable conductive film 1E (indicated by the sign 12Eb in FIG. 14B) including the stretchable conductive layer 3, the stretchable protection layer 6 formed in only a part of one surface of the stretchable conductive layer 3, and the hot-melt adhesive agent layer 4 formed on the other surface of the stretchable conductive layer 3 is placed in a state of being attached to the textile fabric 50.

When the stretchable protection layer 6 is formed in only a part of the surface of the stretchable conductive layer 3, the exposed stretchable conductive layer can be used as an electrode or wiring. The configuration in which the stretchable protection layer 6 is formed in only a part of the surface of the stretchable conductive layer 3 can be fabricated by cutting out the stretchable protection layer 6 that has been patterned on the stretchable conductive layer 3 in advance.

The configuration in which the stretchable protection film is formed in only a part of the surface of the stretchable conductive layer 3 can also be obtained by attaching the stretchable protection film onto a part of the stretchable conductive layer attached to the textile fabric via the hot-melt adhesive agent layer.

While the embodiments of the present invention have been described in detail, the embodiments are merely specific examples for illustrating the technical content of the present invention. It should be noted that the present invention is not to be interpreted as being limited to the specific examples, and that the scope of the present invention is limited only by the appended claims.

The present application corresponds to Japanese Patent Application No. 2015-233710 filed with the Japan Patent Office on Nov. 30, 2015, the entire content of which is hereby incorporated by reference.

DESCRIPTION OF REFERENCE SIGNS 1, 1A to 1E Stretchable conductive film for textiles
2, 5, 7, 8 Peel film
3 Stretchable conductive layer
4 Hot-melt adhesive agent layer
6 Stretchable protection layer

The invention claimed is:

1. A stretchable conductive film for textiles, comprising:
   a stretchable conductive layer having stretch properties;
   a hot-melt adhesive agent layer formed on one surface of the stretchable conductive layer; and
   a stretchable protection layer having stretch properties and formed on at least a part of a surface of the stretchable conductive layer on an opposite side from the hot-melt adhesive agent layer side, wherein
   the stretchable conductive layer is configured from a conductive composition including an elastomer and a conductive filler filling the elastomer, and
   the stretchable protection layer is configured from a composition including the elastomer that is filled with carbon black.

2. The stretchable conductive film for textiles according to claim 1, further comprising a peel film formed on a surface of the hot-melt adhesive agent layer on an opposite side from the stretchable conductive layer side.

3. The stretchable conductive film for textiles according to claim 1, further comprising:
   a first peel film formed on a surface of the stretchable conductive layer on an opposite side from the hot-melt adhesive agent layer side; and
   a second peel film formed on a surface of the hot-melt adhesive agent layer on an opposite side from the stretchable conductive layer side.

4. The stretchable conductive film for textiles according to claim 1, further comprising:
   a first peel film formed on a surface of the stretchable conductive layer on an opposite side from the hot-melt adhesive agent layer side so as to cover the stretchable protection layer; and
   a second peel film formed on a surface of the hot-melt adhesive agent layer on an opposite side from the stretchable conductive layer side.

5. The stretchable conductive film for textiles according to claim 1, wherein the conductive filler is dendritic.

6. The stretchable conductive film according to claim 5, wherein the conductive filler is a dendritic silver powder.

7. The stretchable conductive film according to claim 5, wherein the conductive filler is a silver-coated copper powder comprising a dendritic copper powder coated with silver.

8. The stretchable conductive film for textiles according to claim 1, wherein the conductive filler has a coil shape.

9. The stretchable conductive film for textiles according to claim 1, wherein the hot-melt adhesive agent layer has a melting point of not more than 130° C., durometer hardness of not more than 95 A, and rupture elongation of not less than 300%.

* * * * *